(12) United States Patent
Perryman et al.

(10) Patent No.: US 11,925,809 B1
(45) Date of Patent: *Mar. 12, 2024

(54) SECURING ANTENNAS TO WEARABLE ARTICLES

(71) Applicant: Curonix LLC, Pompano Beach, FL (US)

(72) Inventors: Gary Perryman, Pompano Beach, FL (US); Benjamin Speck, Pompano Beach, FL (US)

(73) Assignee: Curonix LLC, Pompano Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/688,881

(22) Filed: Mar. 7, 2022

Related U.S. Application Data

(63) Continuation of application No. 16/408,524, filed on May 10, 2019, now Pat. No. 11,266,841.

(60) Provisional application No. 62/679,151, filed on Jun. 1, 2018.

(51) Int. Cl.
*A61N 1/372* (2006.01)
*H01Q 1/27* (2006.01)
*H01Q 1/38* (2006.01)

(52) U.S. Cl.
CPC ......... *A61N 1/37229* (2013.01); *H01Q 1/273* (2013.01); *H01Q 1/38* (2013.01)

(58) Field of Classification Search
CPC ... A61N 1/37229; A61N 1/375; A61N 1/3787
See application file for complete search history.

(56) References Cited

U.S. PATENT DOCUMENTS

| 2005/0182389 A1 | 8/2005 | LaPorte et al. |
| 2005/0203584 A1 | 9/2005 | Twetan et al. |
| 2009/0130995 A1 | 5/2009 | Wang |
| 2010/0010565 A1 | 1/2010 | Lichtenstein |

(Continued)

FOREIGN PATENT DOCUMENTS

| WO | WO 2012/138782 | 10/2012 |
| WO | WO 2013/019757 | 2/2013 |

(Continued)

*Primary Examiner* — James M Kish
*Assistant Examiner* — Jessica L Mullins
(74) *Attorney, Agent, or Firm* — MASCHOFF BRENNAN

(57) ABSTRACT

A method of securing an antenna assembly to a wearable article includes positioning a template carrying a first antenna at a desired position on the wearable article worn on a body of a patient. The desired position is in proximity to a wireless tissue stimulator implanted within the body. The method further includes marking a location of the desired position of the template against the wearable article, securing a first attachment feature to the wearable article at a mark located at the desired position, and attaching the antenna assembly to the wearable article at the first attachment feature. The antenna assembly includes a second antenna configured to send a signal carrying electrical energy to the wireless tissue stimulator and a housing carrying the second antenna. The housing includes a second attachment feature configured to engage the first attachment feature for positioning the second antenna adjacent the body.

20 Claims, 13 Drawing Sheets

(56) References Cited

U.S. PATENT DOCUMENTS

| | | | |
|---|---|---|---|
| 2014/0180365 A1* | 6/2014 | Perryman | A61N 1/321 |
| | | | 607/60 |
| 2016/0209868 A1 | 7/2016 | Hartman et al. | |
| 2019/0001139 A1 | 1/2019 | Mishra et al. | |

FOREIGN PATENT DOCUMENTS

| WO | WO 2013/025632 | 2/2013 |
|---|---|---|
| WO | WO 2013/040549 | 3/2013 |
| WO | WO 2012/103519 | 3/2014 |

* cited by examiner

SECURING ANTENNAS TO WEARABLE ARTICLES

CROSS-REFERENCE TO RELATED APPLICATIONS

This application is a continuation of U.S. application Ser. No. 16/408,524, filed May 2019, now allowed, which claims the benefit of U.S. Provisional Application No. 62/679,151, filed Jun. 1, 2018, and titled "Securing Antennas to Wearable Articles." The complete disclosures of all of the above patent applications are hereby incorporated by reference in their entirety for all purposes.

TECHNICAL FIELD

This disclosure relates to securing antennas to wearable articles, such as antennas configured to send electrical energy to tissue stimulators implanted within a patient's body.

BACKGROUND

Modulation of tissue within the body by electrical stimulation has become an important type of therapy for treating chronic, disabling conditions, such as chronic pain, problems of movement initiation and control, involuntary movements, dystonia, urinary and fecal incontinence, sexual difficulties, vascular insufficiency, and heart arrhythmia. For example, an external antenna can be used to send electrical energy to electrodes on an implanted tissue stimulator that can pass pulsatile electrical currents of controllable frequency, pulse width, and amplitudes to a tissue. In order to achieve adequate electrical communication between the external antenna and the implanted tissue stimulator, the antenna must be optimally positioned against the patient's body in a secure manner.

SUMMARY

In general, this disclosure relates to securing antennas to wearable articles, such as articles of clothing and accessories. Such antennas may be configured to send electrical energy to tissue stimulators implanted within a patient's body for delivering electrical therapy to tissues within the body.

In one aspect, an antenna assembly includes an antenna configured to send a signal carrying electrical energy to a wireless tissue stimulator implanted within a body and a housing carrying the antenna. The housing includes a first attachment feature configured to engage a second attachment feature on a wearable article for positioning the antenna adjacent the body on which the wearable article is worn.

Embodiments may provide one or more of the following features.

In some embodiments, the antenna is configured to receive energy from a pulse generator.

In some embodiments, the signal is an RF signal, and the antenna is configured to send the RF signal at a frequency range of about 100 kHz to about 5 GHz.

In some embodiments, the antenna is configured to receive data from the wireless tissue stimulator.

In some embodiments, the antenna assembly includes a flexible circuit board to which the antenna is secured.

In some embodiments, the flexible circuit board includes multiple elongate slots.

In some embodiments, the flexible circuit board is configured to allow passage of the first attachment feature through the housing.

In some embodiments, the antenna is spaced apart from the first attachment feature.

In some embodiments, the antenna is formed as a flat, flexible layer of metal.

In some embodiments, the antenna assembly further includes multiple first attachment features that are configured to respectively engage multiple second attachment features on the wearable article.

In some embodiments, the multiple first attachment features defines a first pattern that aligns with a second pattern formed by the multiple second attachment features.

In some embodiments, the first attachment feature includes a pop rivet snap fastener.

In some embodiments, the first attachment feature includes a hook and loop fastener strip, a magnet, a friction ring, a pin, a hanging slot, or a friction clasp.

In some embodiments, the wearable article includes an upper body clothing article, a lower body clothing article, a whole body clothing article, or an accessory item.

In some embodiments, the housing includes a sleeve.

In some embodiments, the housing is made of a flexible material.

In some embodiments, the housing is made of a molded fabric.

In some embodiments, the housing includes a polymer made of one or more of silicone, polyurethane, and acrylonitrile butadiene styrene (ABS).

In some embodiments, the housing includes a rigid container.

In another aspect, a tissue stimulation system includes a pulse generator and an antenna assembly. The antenna assembly includes an antenna configured to receive electrical energy from the pulse generator and configured to send a signal carrying the electrical energy to a wireless tissue stimulator implanted within a body. The antenna assembly further includes a housing carrying the antenna. The housing includes a first attachment feature by which the antenna assembly can be secured to a wearable article for positioning the antenna adjacent the body on which the wearable article. The tissue stimulation system further includes a second attachment feature configured to be attached to the wearable article and configured to engage the first attachment feature for securing the antenna assembly to the wearable article.

In another aspect, a method of securing an antenna assembly to a wearable article includes positioning a template carrying a first antenna at a desired position on the wearable article worn on a body of a patient. The desired position is in proximity to a wireless tissue stimulator implanted within the body. The method further includes marking a location of the desired position of the template against the wearable article, securing a first attachment feature to the wearable article at a mark located at the desired position, and attaching the antenna assembly to the wearable article at the first attachment feature. The antenna assembly includes a second antenna configured to send a signal carrying electrical energy to the wireless tissue stimulator implanted within the body and includes a housing carrying the second antenna. The housing includes a second attachment feature configured to engage the first attachment feature on the wearable article for positioning the second antenna adjacent the body on which the wearable article is worn.

Embodiments may provide one or more of the following features.

In some embodiments, the method further includes operating the first antenna to send an initial signal carrying initial electrical energy to the wireless tissue stimulator implanted within the body.

In some embodiments, the method further includes moving the template to the desired position against the wearable article based on detection of a suitable stimulation profile at the wireless tissue stimulator by the patient.

In some embodiments, the method further includes removing the template from the wearable article.

DETAILED DESCRIPTION

Figure 1:
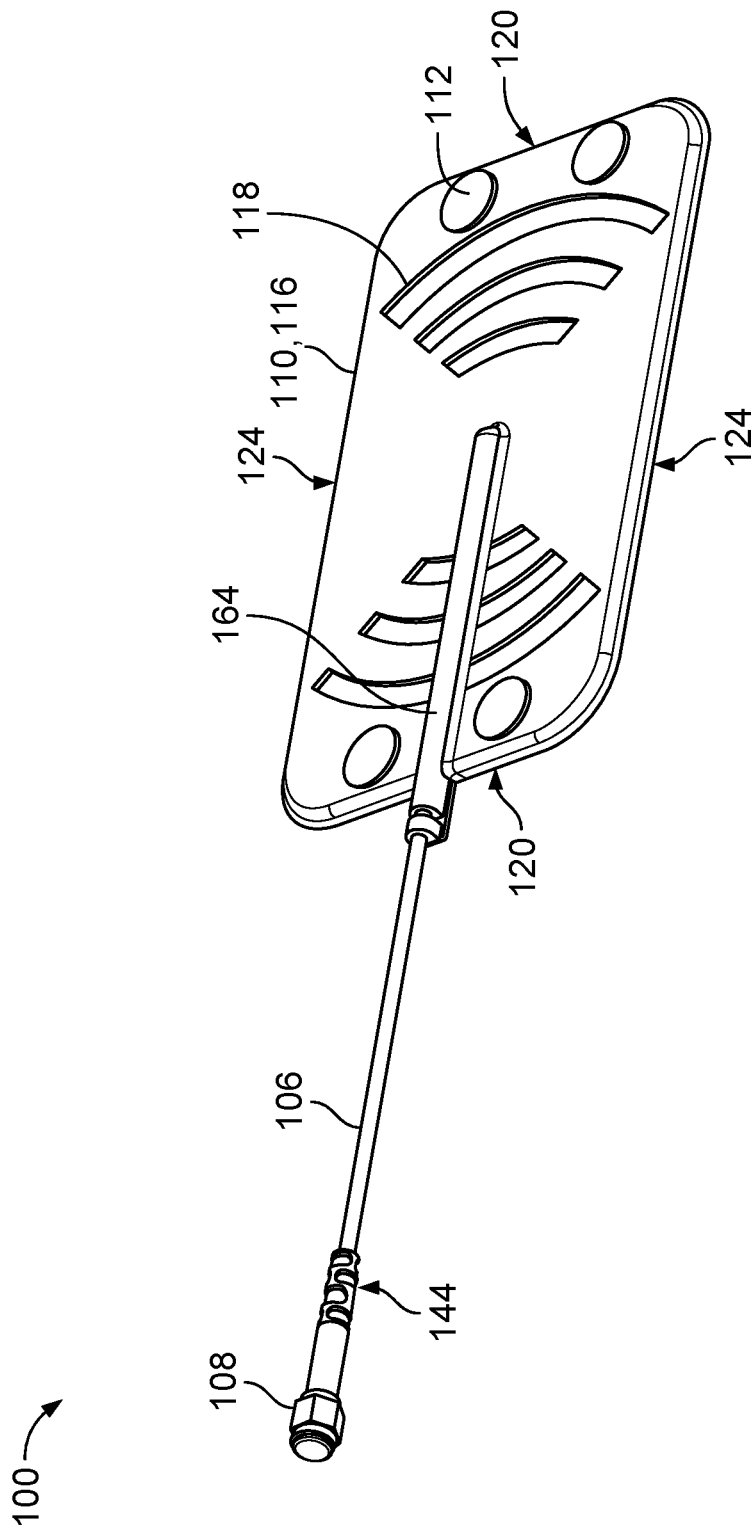
FIG. 1 is a perspective view of an antenna assembly.
Figure 2:
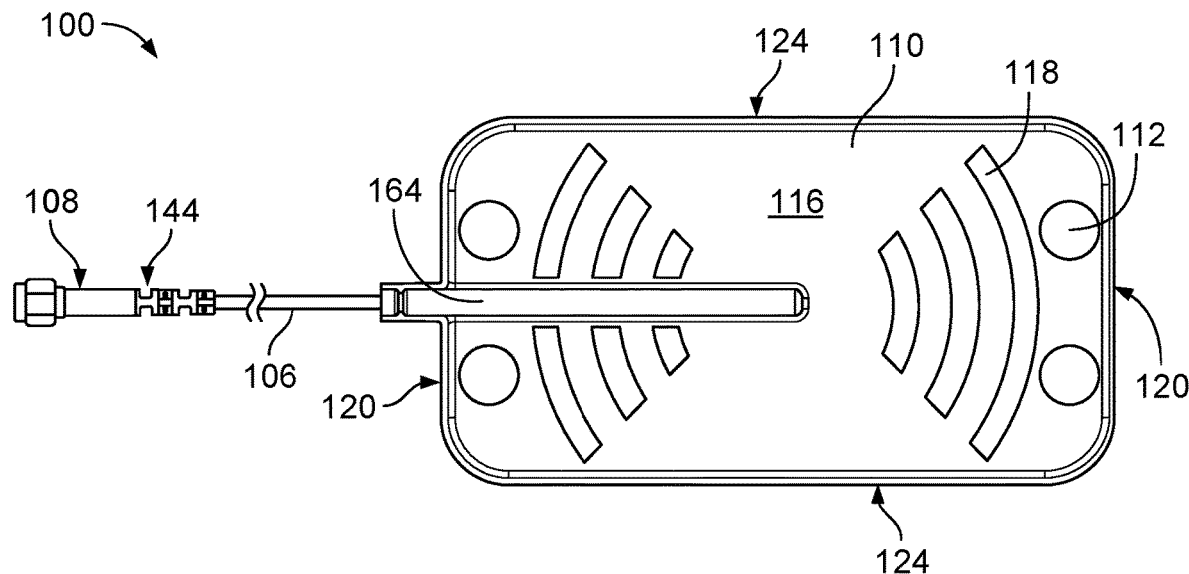
FIG. 2 is a top view of the antenna assembly of FIG. 1.
Figure 3:
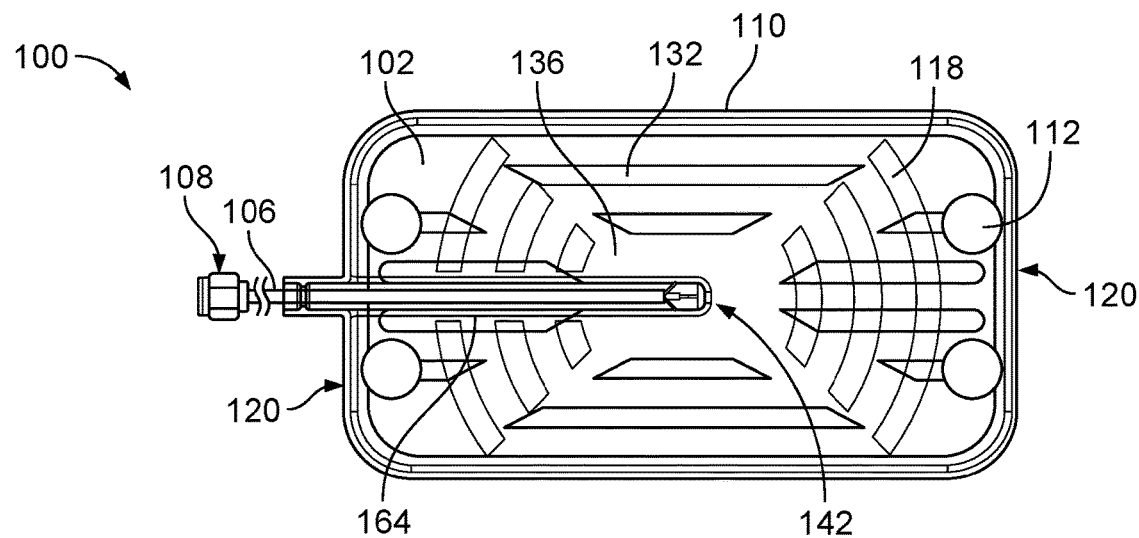
FIG. 3 is a top view of the antenna assembly of FIG. 1, with a portion of a sleeve of the antenna assembly shown as transparent for illustration of internal components.
Figure 4:
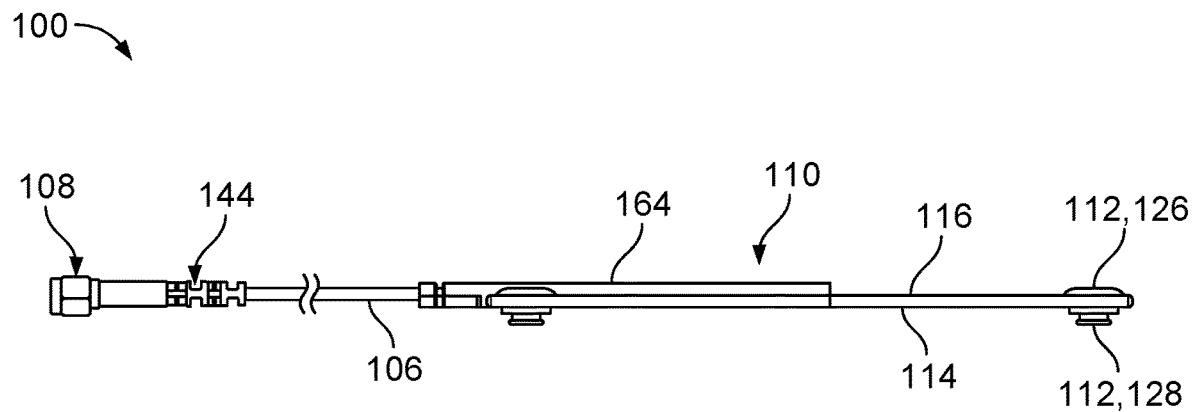
FIG. 4 is a side view of the antenna assembly of FIG. 1.
Figure 5:
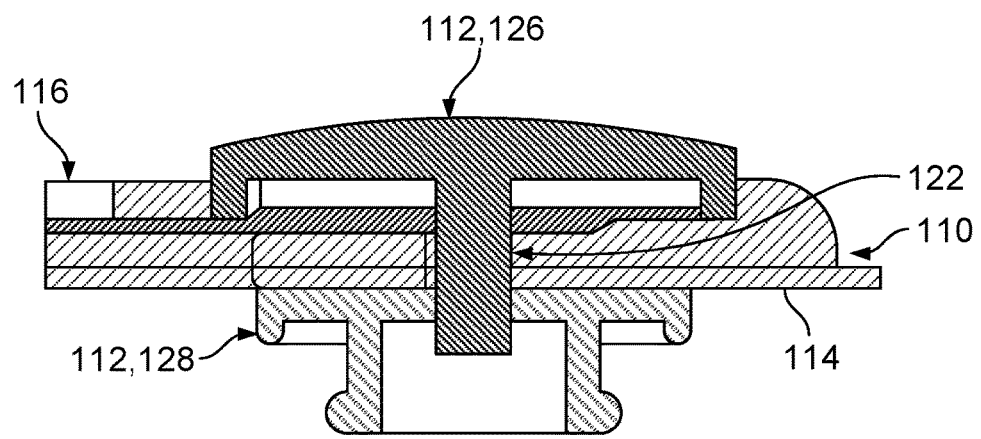
FIG. 5 is an enlarged, side cross-sectional view of a fastener of the antenna assembly of FIG. 1.

FIGS. 1-4 illustrate various views of an antenna assembly 100 designed to be secured to a wearable article disposed along a skin surface of a patient for communicating with a wireless tissue stimulator implanted within the patient's body to deliver electrical therapy to tissues within the patient's body. Example wearable articles include upper body clothing articles (e.g., shirts, sweaters, and jackets), lower body clothing articles (e.g., pants, shorts, and skirts), full body clothing articles (e.g., dresses, overalls, and rompers), and accessory items (e.g., belts, suspenders, hats, braces, scarves, and compression sleeves). Because the antenna assembly 100 can be attached directly to the wearable article, the patient can refrain from obtaining a separate attachment piece (e.g., an elastic accessory belt) that may otherwise be dedicated solely to and needed for attaching such an antenna assembly to a wearable article. The antenna assembly 100 includes a printed circuit board (PCB) 102, an antenna 104 disposed along the PCB 102, a cable 106 in communication with the antenna 104, a connector 108 by which the antenna assembly 100 can be attached to a pulse generator (e.g., a hand-held pulse generator), a sleeve 110 that houses the PCB 102 and the antenna 104, and multiple fasteners 112 carried by the sleeve 110.

The sleeve 110 has a thin, generally flat, low profile and is made of a flexible fabric that allows for easy manipulation (e.g., bending) of the antenna assembly 100 and easy attachment of the antenna assembly 100 to the wearable article. The sleeve 110 is formed to surround the PCB 102 and the antenna 104 and accordingly includes a flat base 114 and a cover 116. The cover 116 defines a receptacle 164 sized to surround a portion of the cable 106 and defines ornamental design features 118 (e.g., symbols that represent signal waves). The receptacle 164 has a generally tubular shape to accommodate the cable 106. The sleeve 110 (e.g., not including the receptacle 164) typically has a length of about 1 cm to about 20 cm, a width of about 1 cm to about 15 cm, and a height of about 0.1 cm to about 2 cm. The receptacle 164 typically has a length of about 1 cm to about 20 cm and a radius of about 0.05 cm to about 3 cm.

The sleeve 110 is typically made of one or more flexible materials that can be worn comfortably against the body for a prolonged period of time. Example materials from which the sleeve 110 may be made include silicone, polyurethane, ABS, neoprene, and polyester. In some embodiments, the material is a foam material. In some embodiments, the material is an antimicrobial material. In some embodiments, the material is a breathable material that dissipates heat efficiently. In some embodiments, the sleeve 110 is coated with a polymer for preventing water damage and easy cleaning. The sleeve 110 is typically manufactured via one or more processes including molding or heat press. In some embodiments, the sleeve 110 includes a re-closable opening or seam by which the sleeve 110 can be removed from remaining components of the antenna assembly 100 for cleaning of the sleeve 110.

Figure 6:
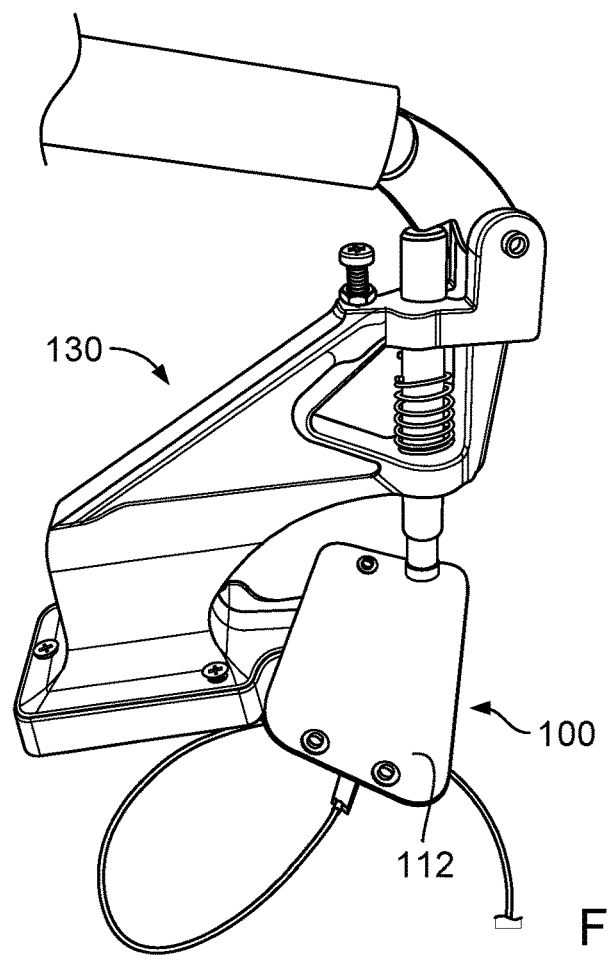
FIG. 6 is a perspective view of a press machine used to secure a fastener to a sleeve of the antenna assembly of FIG. 1.
Figure 7:
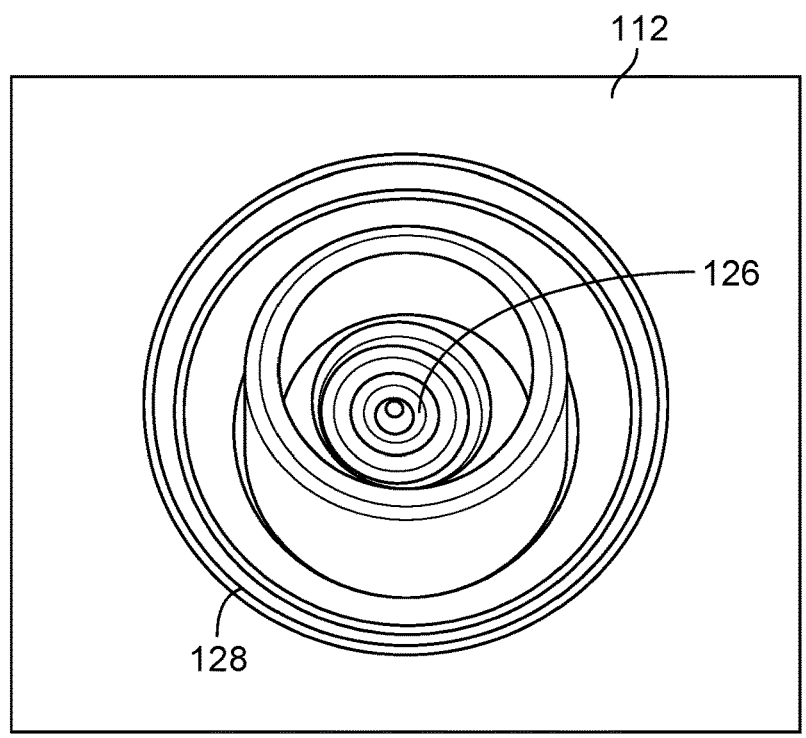
FIG. 7 is a perspective view of an assembled fastener of the antenna assembly of FIG. 1.

Referring to FIGS. 1-5, the sleeve 110 carries four fasteners 112 (e.g., two pop rivet style snap fasteners 112 along each end 120 of the sleeve 110) by which the antenna assembly 100 can be attached to mating fasteners on the wearable article. Accordingly, the sleeve 110 defines four through holes 122 at which the fasteners 112 are respectively located. The through holes 122 are positioned such that the fasteners 112 do not interfere with (e.g., contact) the antenna 104. For example, each through hole 122 is positioned about 0.1 cm to about 3 cm from respective ends 120 of the sleeve 110 and about 0.1 cm to about 3 cm from respective sides 124 of the sleeve 110 such that adjacent fasteners 112 are spaced about 1 cm to about 15 cm from each other. Each fastener 112 includes a male portion 126 (e.g., a stud) and a female portion 128 (e.g., a cap 128) that can be deformed and press fit together using a press machine 130 (e.g., an arbor press), as shown in FIGS. 6 and 7. The fasteners 112 are typically made of one or more materials including ABS, polyethylene terephthalate (PET), or polyethylene (PE).

Figure 8:
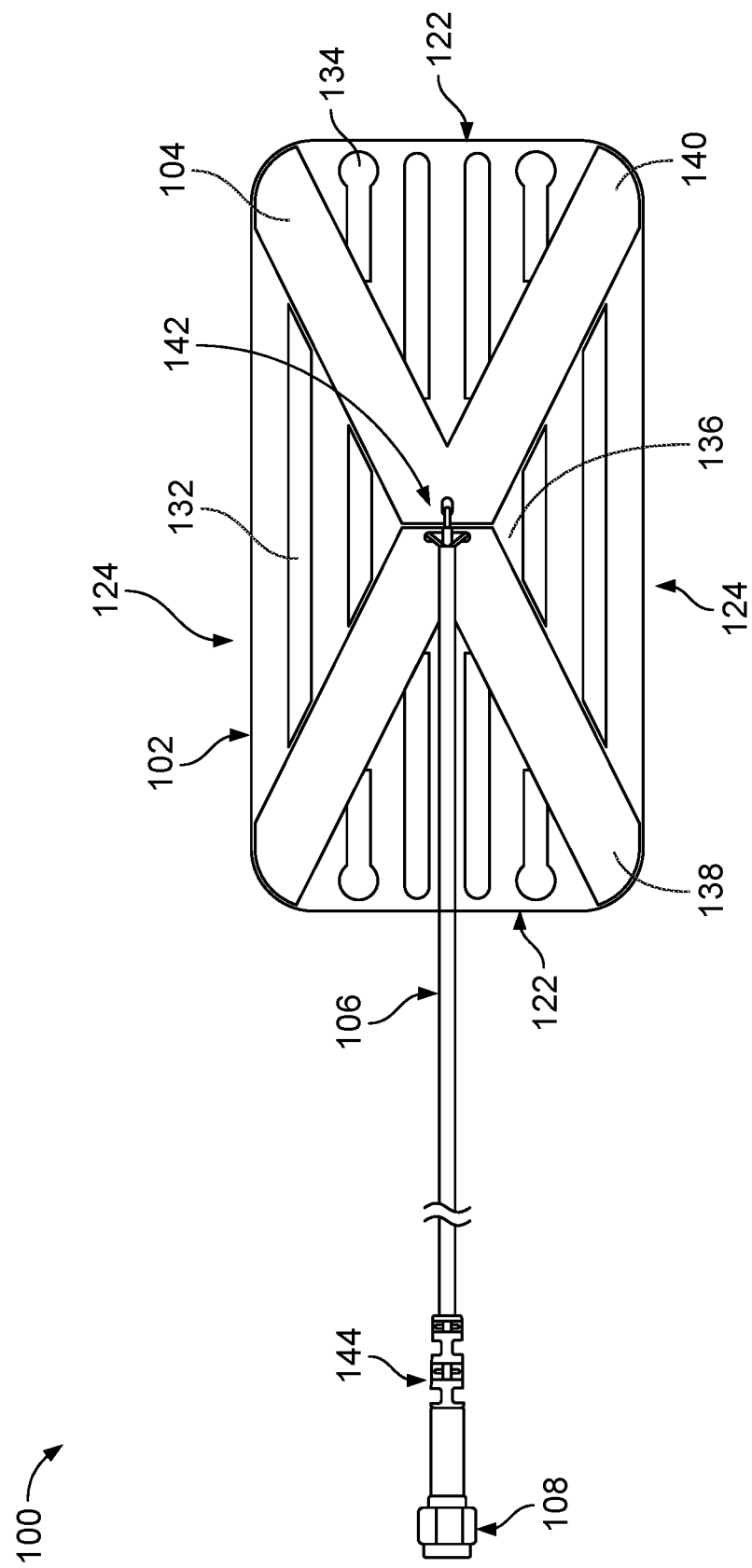
FIG. 8 is a top view of an antenna, a PCB, a cable, and a connector of the antenna assembly of FIG. 1.

Referring to FIG. 8, the PCB 102 is formed as a generally broad, thin, flexible substrate. The PCB 102 defines several elongate slots 132 that contribute to a flexibility of the PCB 102, multiple circular holes 134 that respectively allow passage of the male portions 126 of the fasteners 112, and a central support region 136 formed complementary to a shape of the antenna 104. The PCB 102 typically has a thickness of about 0.025 mm to about 1 mm. The slots 132 typically have a width of about 0.1 cm to about 3 cm and are located so as not to interfere with copper traces along the PCB. The circular holes 134 typically have a width (e.g., a diameter) of about 0.05 cm to about 2 cm. The width of the circular holes 134 is larger than the diameter of the through holes 122 on the sleeve 110 to allow for variable positioning of the through holes 122 on the sleeve 110 (e.g., within a specified tolerance). The circular holes 134 (e.g., and the through holes 122) are positioned such that the fasteners 112 avoid contact with the antenna 104 and with the PCB 102. The PCB 102 is typically made of polyimide.

The antenna 104 is formed as a thin, flexible electrically conductive layer with a shape (e.g., that of an "X") that is generally complementary to the shape of the central support region 136 of the PCB 102. The antenna 104 includes two mirrored portions 138, 140 to which an end region 142 of the cable 106 is attached for communicating signals to and from the antenna 104. While the two portions 138, 140 both include copper, the two portions 138, 140 are not connected electrically. The antenna 104 typically has a thickness of about 0.02 mm to about 0.2 mm. As will be discussed in more detail below, the antenna 104 (e.g., a patch antenna, a slot antenna, or a dipole antenna) is in electrical communication with the pulse generator via the cable 106 and the connector 108 and is designed to receive a signal from the pulse generator and to transmit a radio frequency (RF) signal (e.g., in a range of about 100 kHz to about 5 GHz) to the wireless tissue stimulator implanted within the patient's body. The cable 106 is flexible and has a length of about 3 cm to about 50 cm. The connector 108 is a molded, plastic component including a cutout pattern 144 that imparts flexibility to the connector 108.

Figure 9:
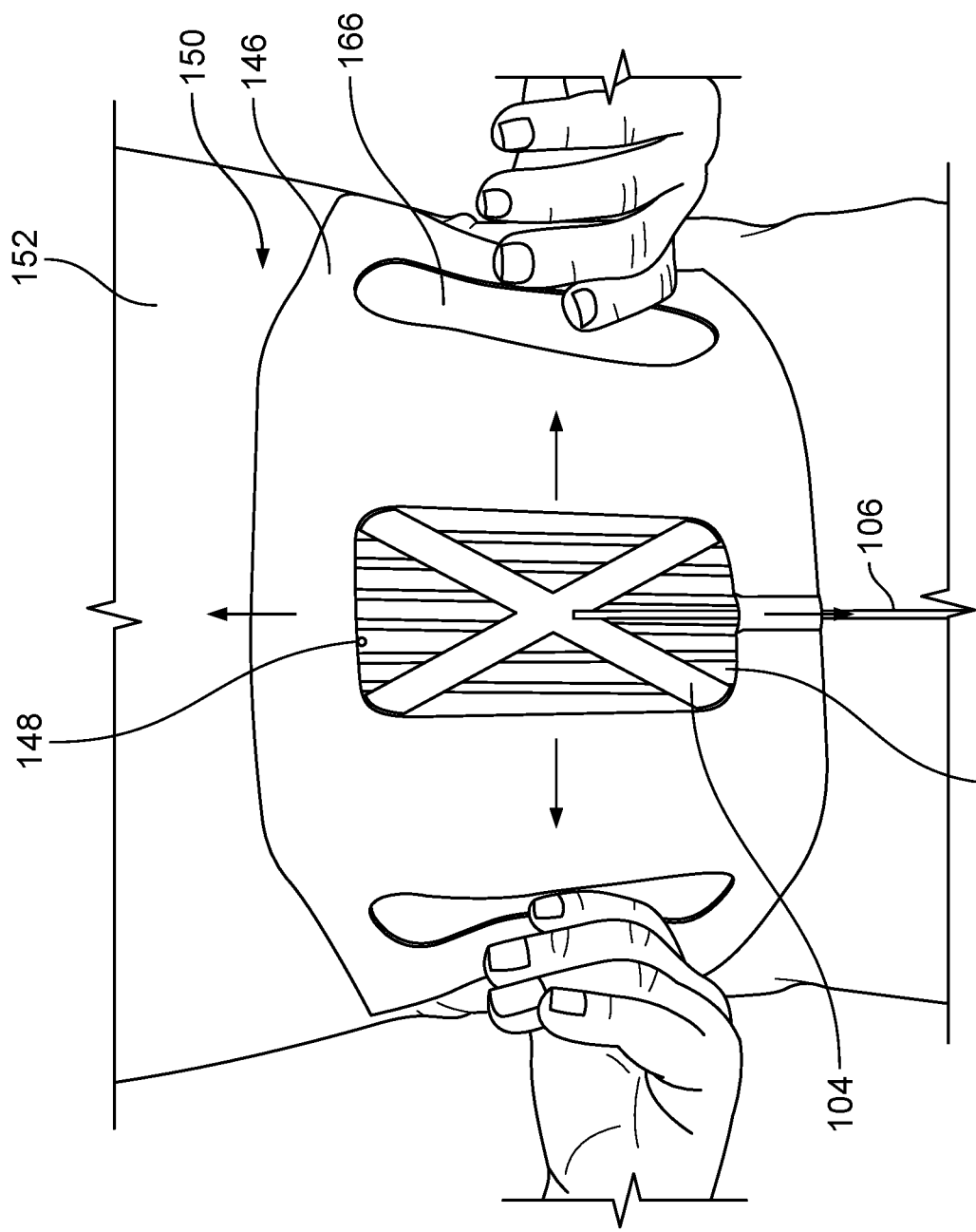
FIGS. 9-14 illustrate a method of securing the antenna assembly of FIG. 1 to a wearable article.

For operation of a tissue stimulation system that includes the antenna assembly 100, the antenna assembly 100 can be attached to an article worn by the patient at a point of care. In some examples, the patient, a medical practitioner, or a technician (e.g., a field technician) can use a template 150 to attach the antenna assembly 100 to the article, as shown in FIG. 9. The template 150 includes a PCB 102, an antenna 104, a cable 106, a connector 108, and a flexible sheet 146 of material that supports these components. The flexible sheet 146 defines four holes 148 that are positioned to respectively align with the circular holes 134, the through holes 120, and the fasteners 112 carried therein. The flexible sheet 146 also defines two opposing slots 166 that allow for gripping edges of the flexible sheet 146.

The patient can select a wearable article 152 (e.g., a shirt, in the example of FIGS. 9-14) that fits snuggly against the body for use with the template 150 and the tissue stimulation system. The template 150 is then placed against the wearable article 152 at a location in proximity to an underlying wireless tissue stimulator implanted within the patient's body. A pulse generator 154 (e.g., an RF pulse generator) of the tissue stimulation system is then attached to the connector 108 of the template 150 and turned on to transmit signals via the antenna 104 to the tissue stimulator. While the pulse generator 154 is transmitting signals, a position of the template 150 can be adjusted along the wearable article 152 until a desired or acceptable stimulation profile at the tissue stimulator is detected by the patient.

Figure 10:
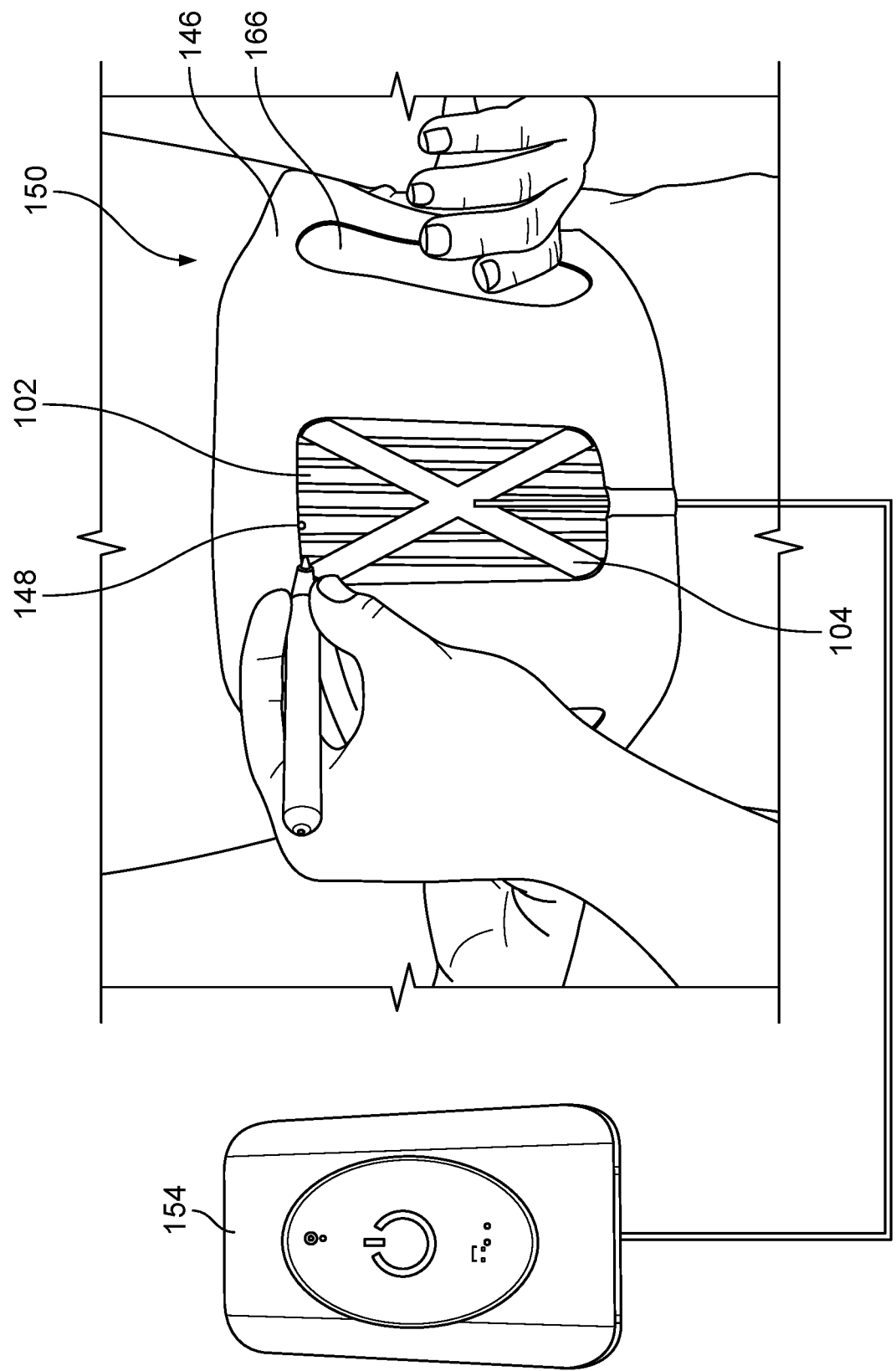
Figure 13:
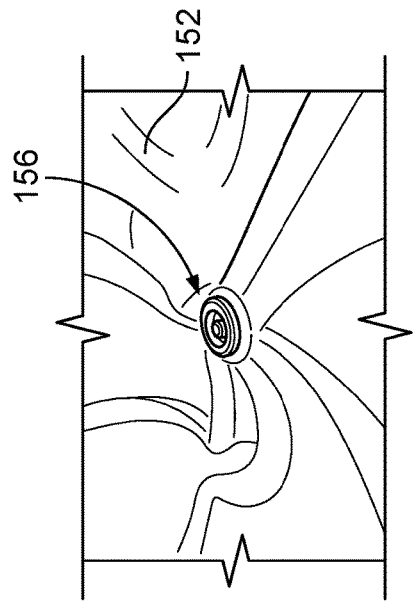
Figure 14:
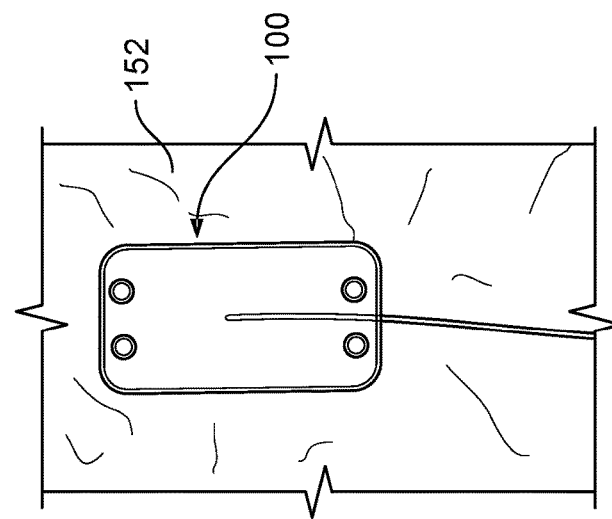
Figure 11:
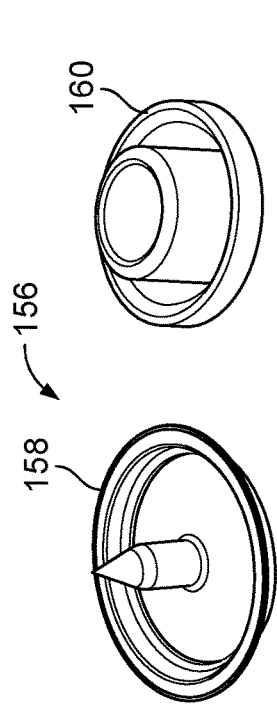
Figure 12:
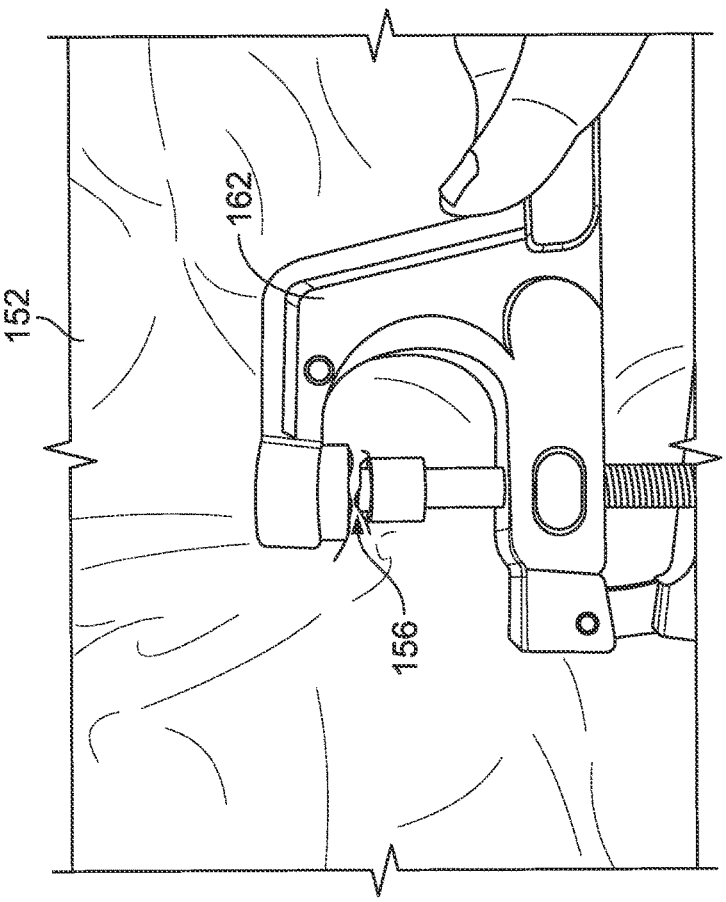

Referring to FIG. 10, the pulse generator is then turned off, and locations of the holes 148 are marked on the wearable article 152 with an ink utensil while the template 150 is still positioned at the desired location. Referring to FIG. 11, fasteners 156 (e.g., pop rivet style snap fasteners) that are designed to mate with the fasteners 112 are then selected for attachment to the wearable article 152 at the holes 148. Each fastener 156 includes a male portion 158 (e.g., a stud) designed to pierce the fabric wearable article 152 and a female portion 160 (e.g., a cap). Referring to FIG. 12, the male portion 158 is passed through the wearable article 152 at a mark corresponding to a hole 148, and the male and female portions 158, 160 are press fitted together (e.g., sandwiching the shirt therebetween) at the mark with a press machine 162 to provide an attached fastener 156, as shown in FIG. 13. Additional fasteners 156 are similarly attached at the remaining marks corresponding to the holes 148 to provide a pattern at which the antenna assembly 100 can be repeatedly attached to the wearable article 152 for prolonged use, as shown in FIG. 14, and detached as desired. Once the antenna assembly 100 is attached to the wearable article 152, the tissue stimulation system can be operated to deliver electrical therapy to the patient according to appropriate protocols. In some examples, the fasteners 156 are not permanently attached to the wearable article 152 and can be removed from the wearable article 152 (e.g., or another wearable article) using a dedicated tool without damaging the wearable article 152. In general, the fasteners 156 can be attached to wearable articles made of various materials, such as cotton, polyester, silk, linen, elastane, wool, or a blend. In some examples, the wearable article 152 and the fasteners 156 are provided as a components of a kit that includes the tissue stimulation system.

Figure 15:
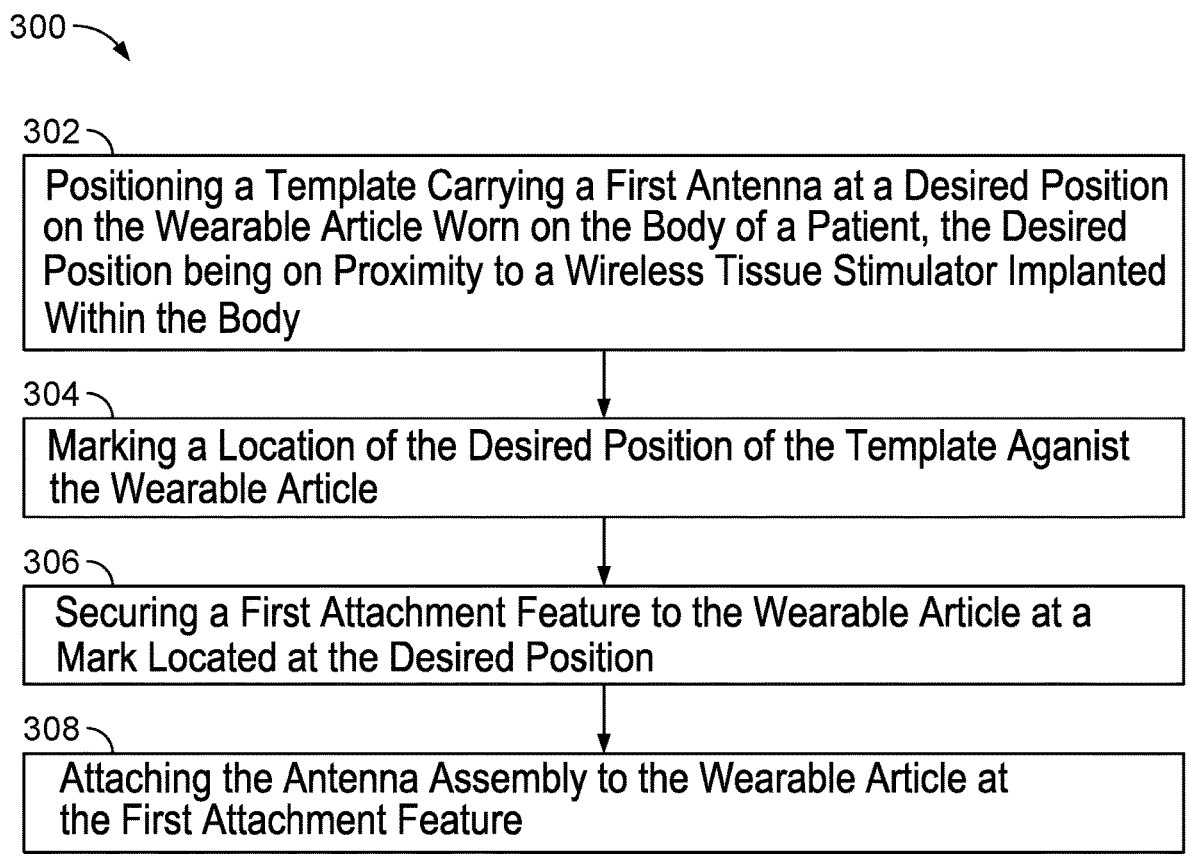
FIG. 15 is a flowchart of a method of securing the antenna assembly of FIG. 1 to a wearable article.
Figure 17A:
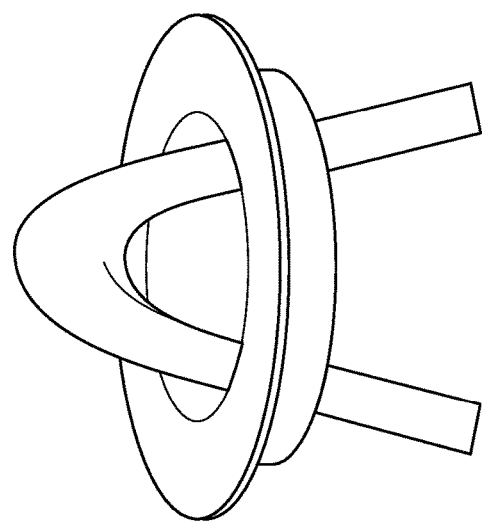
FIGS. 17A to 17E provide perspective views of various attachment features that can be used on an antenna assembly.
Figure 17B:
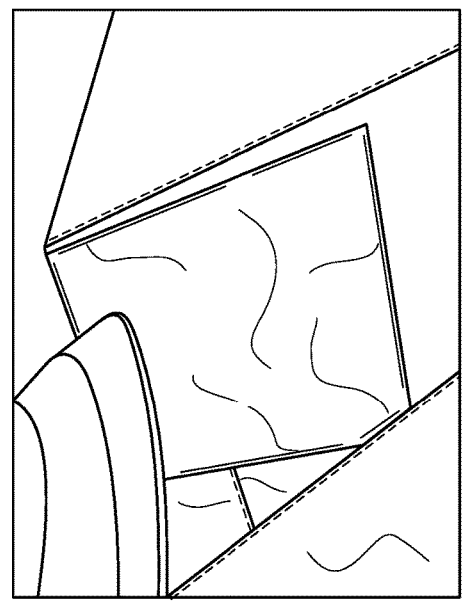

FIG. 15 provides a flowchart that illustrates a method 300 of securing (e.g., attaching) an antenna assembly (e.g., the antenna assembly 100) to a wearable article (e.g., the wearable article 152). In some examples, the method includes positioning a template (e.g., the template 150) carrying a first antenna (e.g., the antenna 104) at a desired position on the wearable article worn on a body of a patient, the desired position being in proximity to a wireless tissue stimulator implanted within the body (302). In some examples, the method 300 further includes marking a location of the desired position of the template against the wearable article (304). In some examples, the method further includes securing a first attachment feature (e.g., the fastener 112) to the wearable article at a mark located at the desired position (306). In some examples, the method further includes attaching the antenna assembly to the wearable article at the first attachment feature (308).

Figure 16:
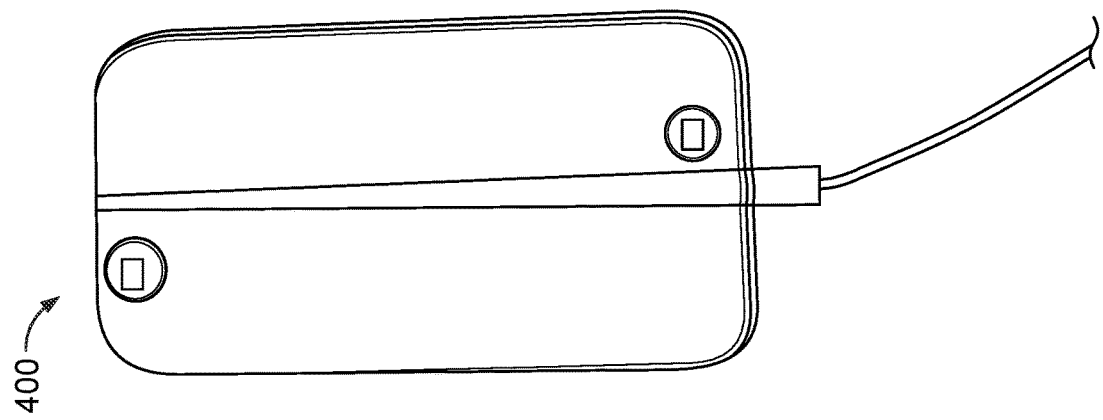
FIG. 16 is a top view of an antenna assembly.
Figure 17C:
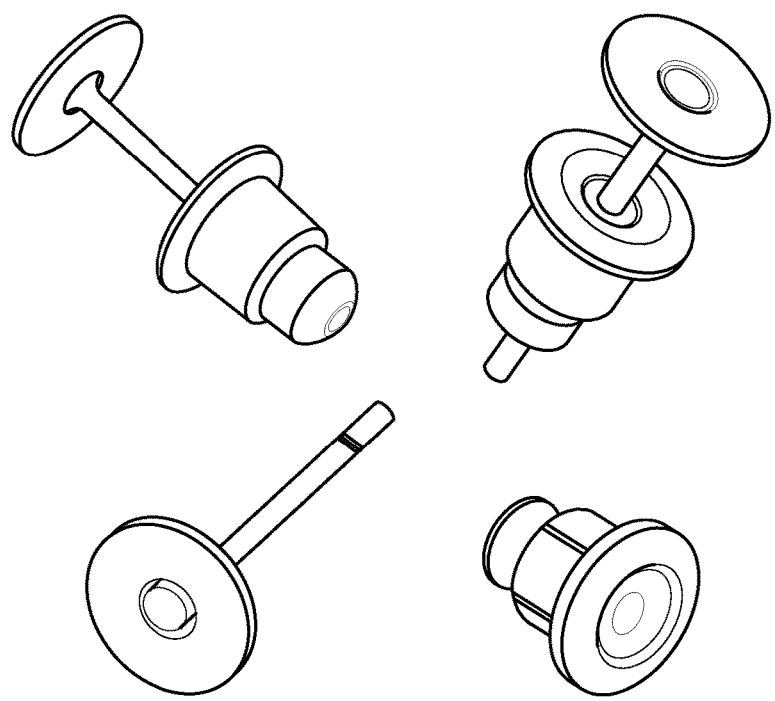
Figure 17D:
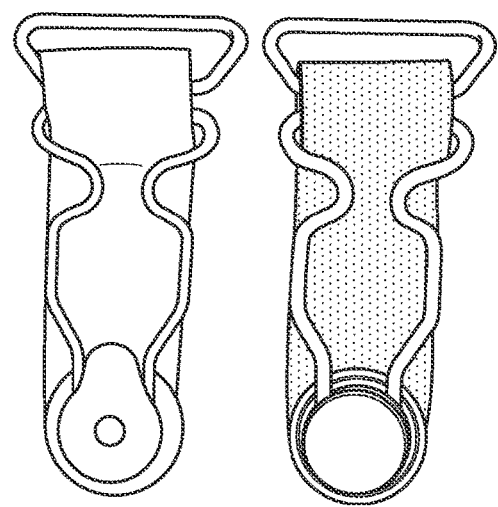
Figure 17E:
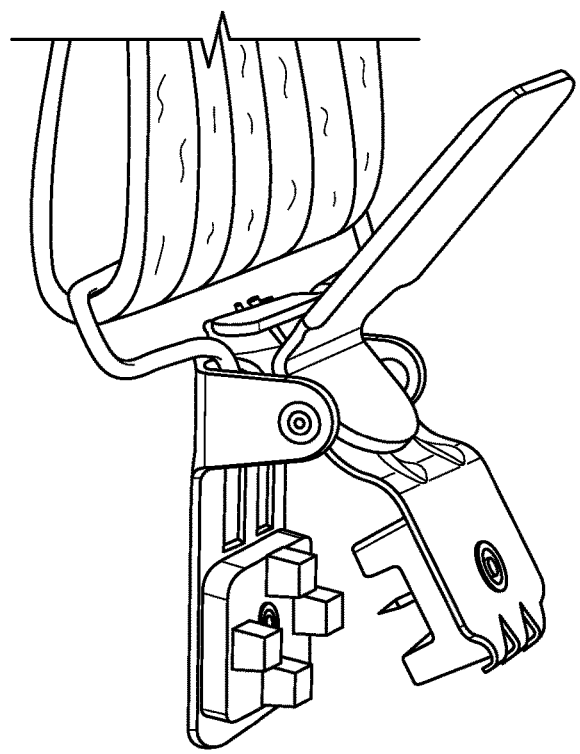

While the antenna assembly 100 has been described and illustrated as including certain dimensions, sizes, shapes, materials, arrangements, and configurations, in some embodiments, antenna assemblies that are similar in structure and function to the antenna assembly 100 may include different dimensions, sizes, shapes, materials, arrangements, or configurations. For example, FIG. 16 illustrates an antenna assembly 400 that includes a different number of fasteners 112 (e.g., two fasteners 112). The antenna assembly 400 is otherwise similar in structure and function to the antenna assembly 100.

While the fasteners 112, 156 have been described and illustrated as pop rivet style snap fasteners, in some embodiments, an antenna assembly that is otherwise similar in structure and function to the antenna assembly 100 may include a different type of fastener. For example, in some embodiments, an antenna assembly may include hook and loop type fasteners (e.g., sewn, adhered, or snapped into the sleeve and the wearable article), magnet style fasteners (e.g., embedded, sewn, or ironed into the sleeve and the wearable article or a piece of fabric attached to the wearable article) In some embodiments, as shown in FIG. 17, the antenna assembly may include friction ring type fasteners (e.g., including a hole through which a fabric can be passed and a mating ring that holds the fabric in place, referring (a)), a pocket formed to be ironed or sewn onto the wearable article and to hold the antenna assembly against the wearable article (referring to (b)), pin type fasteners (referring to (c)), rails for holding a rigid antenna assembly, hanging slots and clasps (referring to (d)), and friction clasps (referring to (e)).

While the antenna assembly 100 has been described and illustrated as including the fabric sleeve 110, in some embodiments, an antenna assembly that is otherwise similar in function to the antenna assembly 100 may include a rigid sleeve or alternatively include another type of rigid housing or container.

Figure 18:
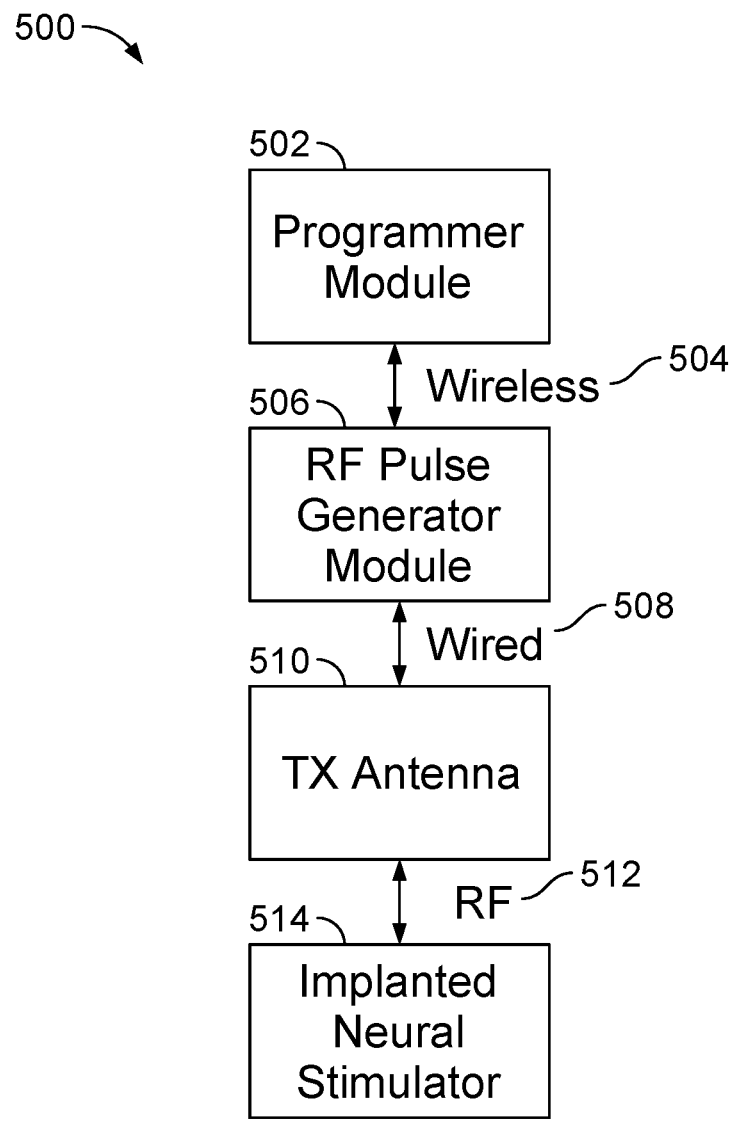
FIG. 18 is a system block diagram of a tissue stimulator system including the antenna assembly of FIG. 1.

In some embodiments, any of the above-discussed antenna assemblies may be provided as part of a tissue stimulation system, such as a neural stimulation system 500, shown in FIG. 18. The neural stimulation system 500 may be used to send electrical stimulation to targeted nerve tissue by using remote radio frequency (RF) energy without cables and without inductive coupling to power the tissue stimulator 514, provided as a passive stimulator. In some examples, the targeted nerve tissues may be in the spinal column and include the spinothalamic tracts, dorsal horn, dorsal root ganglia, dorsal roots, dorsal column fibers, and peripheral nerves bundles leaving the dorsal column or brainstem, as well as any cranial nerves, abdominal, thoracic, or trigeminal ganglia nerves, nerve bundles of the cerebral cortex, deep brain and any sensory or motor nerves.

The neural stimulation system 500 may include a controller module (e.g., an RF pulse generator module) and the passive tissue stimulator 514, which includes one or more dipole antennas, circuit components, and electrodes that can contact targeted neural tissue to provide tissue stimulation. The RF pulse generator module may include an antenna and may be configured to transfer energy from the module antenna to the implanted antennas. The circuit components may be configured to generate electrical pulses suitable for neural stimulation using the transferred energy and to supply the electrical pulses to the electrodes so that the pulses are applied to the neural tissue. For instance, the circuit components may include wave conditioning circuitry that rectifies the received RF signal (for example, using a diode rectifier), transforms the RF energy to a low frequency signal suitable for the stimulation of neural tissue, and presents the resulting waveform to an electrode array. The circuit components may also include circuitry for communicating information back to the RF pulse generator module to facilitate a feedback control mechanism for stimulation parameter control. For example, the tissue stimulator 514 may send to the RF pulse generator module a stimulus feedback signal that is indicative of parameters of the electrical pulses, and the RF pulse generator module may employ the stimulus feedback signal to adjust parameters of the signal sent to the neural stimulator.

Still referring to FIG. 18, neural stimulation system 500 includes a programmer module 502, an RF pulse generator module 506, the antenna assembly 100 including the transmit (TX) antenna 104 (e.g., a patch antenna, slot antenna, or a dipole antenna), and the tissue stimulator 514. The programmer module 502 may be a computer device, such as a smart phone, running a software application that supports a wireless connection 504, such as Bluetooth® The application can enable the user to view the system status and diagnostics, change various parameters, increase/decrease the desired stimulus amplitude of the electrode pulses, and adjust feedback sensitivity of the RF pulse generator module 506, among other functions.

The RF pulse generator module 506 may include communication electronics that support the wireless connection 504, the stimulation circuitry, and the battery to power the generator electronics. In some implementations, the RF pulse generator module 506 includes the TX antenna embedded into its packaging form factor while, in other implementations, the TX antenna is connected to the RF pulse generator module 506 through a wired connection 508 or a wireless connection (not shown). The TX antenna 104 may be coupled directly to tissue to create an electric field that powers the tissue stimulator 514. The TX antenna 104 communicates with the implanted tissue stimulator 514 through an RF interface. For instance, the TX antenna 104 radiates an RF transmission signal that is modulated and encoded by the RF pulse generator module 104. The tissue stimulator 514 contains one or more antennas 106, such as dipole antenna(s), to receive and transmit through RF interface 512. In particular, the coupling mechanism between antenna 104 and the one or more antennas 106 on the tissue stimulator 514 is electrical radiative coupling and not inductive coupling. In other words, the coupling is through an electric field rather than a magnetic field.

Through this electrical radiative coupling, the TX antenna 104 can provide an input signal to the implanted tissue stimulator 514. This input signal contains energy and may contain information encoding stimulus waveforms to be applied at the electrodes 106 of the tissue stimulator 514. In some implementations, the power level of this input signal directly determines an applied amplitude (for example, power, current, or voltage) of the one or more electrical pulses created using the electrical energy contained in the input signal. Within the implanted tissue stimulator 514 are the circuit components 106 for demodulating the RF transmission signal, and the electrodes 106 to deliver the stimulation to surrounding neuronal tissue.

The RF pulse generator module 506 can be implanted subcutaneously, or it can be worn external to the body. When external to the body, the RF generator module 506 can be incorporated into a belt or harness design to allow for electric radiative coupling through the skin and underlying tissue to transfer power and/or control parameters to the tissue stimulator 514. In either event, receiver circuit components 104 internal to the tissue stimulator 514 can capture the energy radiated by the TX antenna 104 and convert this energy to an electrical waveform. The receiver circuit components 404 may further modify the waveform to create an electrical pulse suitable for the stimulation of neural tissue, and this pulse may be delivered to the tissue via the electrodes 108.

In some implementations, the RF pulse generator module 506 can remotely control the stimulus parameters (that is, the parameters of the electrical pulses applied to the neural tissue) and monitor feedback from the wireless tissue stimulator 514 based on RF signals received from the tissue stimulator 514. A feedback detection algorithm implemented by the RF pulse generator module 506 can monitor data sent wirelessly from the implanted tissue stimulator 514, including information about the energy that the tissue stimulator 514 is receiving from the RF pulse generator 506 and information about the stimulus waveform being delivered to the electrodes 108. In order to provide an effective therapy for a given medical condition, the system can be tuned to provide the optimal amount of excitation or inhibition to the nerve fibers by electrical stimulation. A closed loop feedback control method can be used in which the output signals from the implanted tissue stimulator 514 are monitored and used to determine the appropriate level of neural stimulation current for maintaining effective neuronal activation, or, in some cases, the patient can manually adjust the output signals in an open loop control method.

Figure 19:
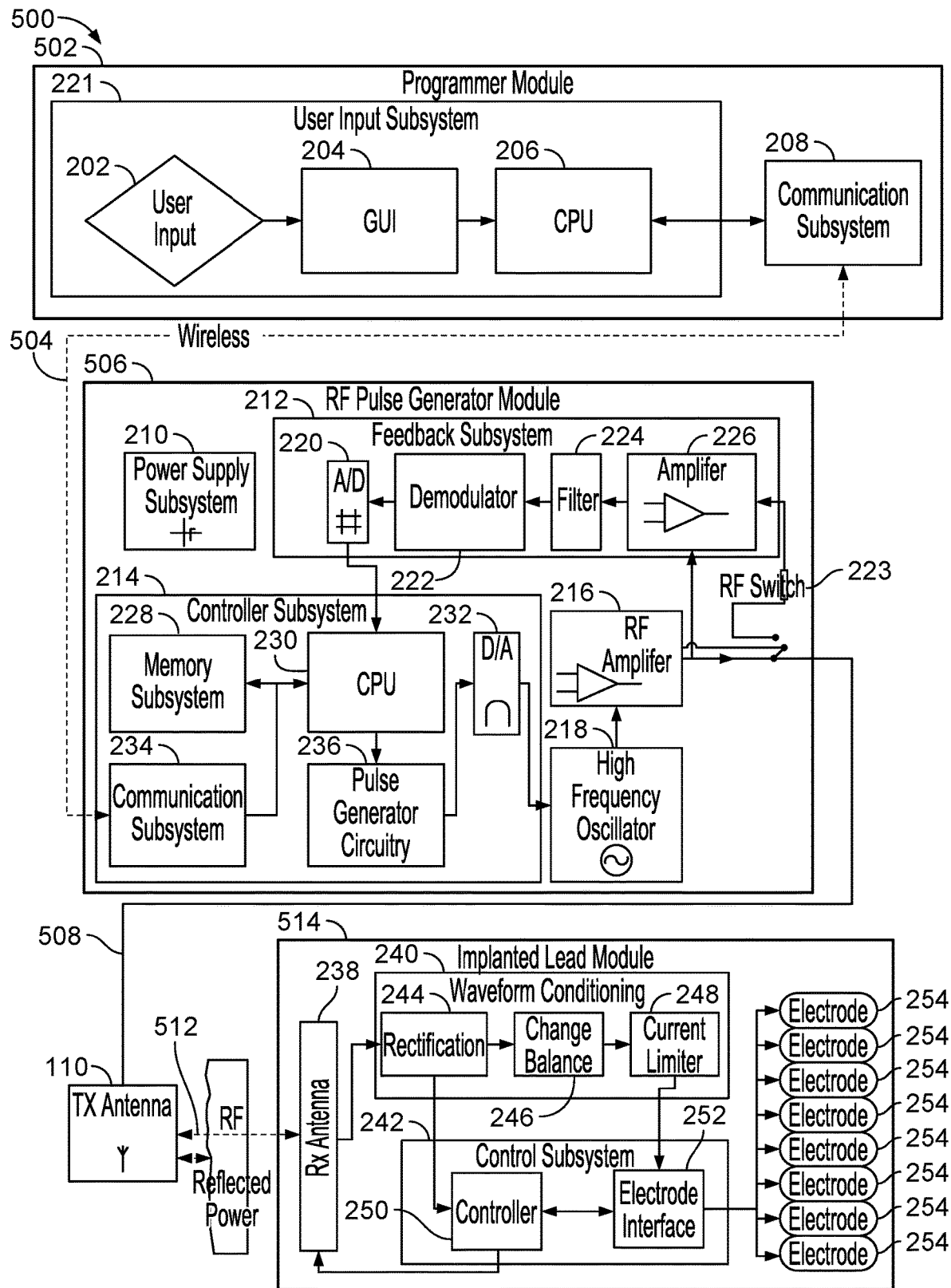
FIG. 19 is a detailed block diagram of the tissue stimulator system of FIG. 18.

FIG. 19 depicts a detailed diagram of the neural stimulation system 500. As depicted, the programming module 502 may include user input system 202 and communication subsystem 208. The user input system 221 may allow various parameter settings to be adjusted (in some cases, in an open loop fashion) by the user in the form of instruction sets. The communication subsystem 208 may transmit these instruction sets (and other information) via the wireless connection 504, such as Bluetooth or Wi-Fi, to the RF pulse generator module 506, as well as receive data from module 506.

For instance, the programmer module 502, which can be utilized for multiple users, such as a patient's control unit or clinician's programmer unit, can be used to send stimulation parameters to the RF pulse generator module 506. The stimulation parameters that can be controlled may include pulse amplitude, pulse frequency, and pulse width in the ranges of 0 to 20 mA, 0 to 2000 Hz Pulse Width, and 0 to 2 ms, respectively. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

The tissue stimulator 514 or RF pulse generator module 506 may be initially programmed to meet the specific parameter settings for each individual patient during the initial implantation procedure. Because medical conditions or the body itself can change over time, the ability to re-adjust the parameter settings may be beneficial to ensure ongoing efficacy of the neural modulation therapy.

The programmer module 502 may be functionally a smart device and associated application. The smart device hardware may include a CPU 206 and be used as a vehicle to handle touchscreen input on a graphical user interface (GUI) 204, for processing and storing data.

The RF pulse generator module 506 may be connected via wired connection 508 to an external TX antenna 104. Alternatively, both the antenna and the RF pulse generator are located subcutaneously (not shown).

The signals sent by RF pulse generator module 506 to the implanted stimulator 1414 may include both power and parameter-setting attributes in regards to stimulus waveform, amplitude, pulse width, and frequency. The RF pulse generator module 506 can also function as a wireless receiving unit that receives feedback signals from the tissue stimulator 514. To that end, the RF pulse generator module 506 may contain microelectronics or other circuitry to handle the generation of the signals transmitted to the tissue stimulator 514 as well as handle feedback signals, such as those from tissue stimulator 514. For example, the RF pulse generator module 506 may include controller subsystem 214, high-frequency oscillator 218, RF amplifier 216, a RF switch, and a feedback subsystem 212.

The controller subsystem 214 may include a CPU 230 to handle data processing, a memory subsystem 228 such as a local memory, communication subsystem 234 to communicate with programmer module 502 (including receiving stimulation parameters from programmer module), pulse generator circuitry 236, and digital/analog (D/A) converters 232.

The controller subsystem 214 may be used by the patient and/or the clinician to control the stimulation parameter settings (for example, by controlling the parameters of the signal sent from RF pulse generator module 506 to tissue stimulator 514). These parameter settings can affect, for example, the power, current level, or shape of the one or more electrical pulses. The programming of the stimulation parameters can be performed using the programming module 502, as described above, to set the repetition rate, pulse width, amplitude, and waveform that will be transmitted by RF energy to the receive (RX) antenna 238 (e.g., an embodiment of the antenna 106), typically a dipole antenna (although other types may be used), in the wireless implanted tissue stimulator 514. The clinician may have the option of locking and/or hiding certain settings within the programmer interface, thus limiting the patient's ability to view or adjust certain parameters because adjustment of certain parameters may require detailed medical knowledge of neurophysiology, neuroanatomy, protocols for neural modulation, and safety limits of electrical stimulation.

The controller subsystem 214 may store received parameter settings in the local memory subsystem 228, until the parameter settings are modified by new input data received from the programming module 502. The CPU 206 may use the parameters stored in the local memory to control the pulse generator circuitry 236 to generate a stimulus waveform that is modulated by a high frequency oscillator 218 in the range from 300 MHz to 8 GHz. The resulting RF signal may then be amplified by RF amplifier 226 and then sent through an RF switch 223 to the TX antenna 104 to reach through depths of tissue to the RX antenna 238.

In some implementations, the RF signal sent by TX antenna 104 may simply be a power transmission signal used by tissue stimulator 514 to generate electric pulses. In other implementations, a telemetry signal may also be transmitted to the tissue stimulator 514 to send instructions about the various operations of the tissue stimulator 514. The telemetry signal may be sent by the modulation of the carrier signal (through the skin if external, or through other body tissues if the pulse generator module 506 is implanted subcutaneously). The telemetry signal is used to modulate the carrier signal (a high frequency signal) that is coupled onto the implanted antenna(s) 238 and does not interfere with the input received on the same lead to power the implant. In one embodiment the telemetry signal and powering signal are combined into one signal, where the RF telemetry signal is used to modulate the RF powering signal, and thus the implanted stimulator is powered directly by the received telemetry signal; separate subsystems in the stimulator harness the power contained in the signal and interpret the data content of the signal.

The RF switch 223 may be a multipurpose device such as a dual directional coupler, which passes the relatively high amplitude, extremely short duration RF pulse to the TX antenna 104 with minimal insertion loss while simultaneously providing two low-level outputs to feedback subsystem 212; one output delivers a forward power signal to the feedback subsystem 212, where the forward power signal is an attenuated version of the RF pulse sent to the TX antenna 104, and the other output delivers a reverse power signal to a different port of the feedback subsystem 212, where reverse power is an attenuated version of the reflected RF energy from the TX Antenna 104.

During the on-cycle time (when an RF signal is being transmitted to tissue stimulator 514), the RF switch 223 is set to send the forward power signal to feedback subsystem. During the off-cycle time (when an RF signal is not being transmitted to the tissue stimulator 514), the RF switch 223 can change to a receiving mode in which the reflected RF energy and/or RF signals from the tissue stimulator 514 are received to be analyzed in the feedback subsystem 212.

The feedback subsystem 212 of the RF pulse generator module 506 may include reception circuitry to receive and extract telemetry or other feedback signals from tissue stimulator 514 and/or reflected RF energy from the signal sent by TX antenna 104. The feedback subsystem may include an amplifier 226, a filter 224, a demodulator 222, and an A/D converter 220.

The feedback subsystem 212 receives the forward power signal and converts this high-frequency AC signal to a DC level that can be sampled and sent to the controller subsystem 214. In this way the characteristics of the generated RF pulse can be compared to a reference signal within the controller subsystem 214. If a disparity (error) exists in any parameter, the controller subsystem 214 can adjust the output to the RF pulse generator 506. The nature of the adjustment can be, for example, proportional to the computed error. The controller subsystem 214 can incorporate additional inputs and limits on its adjustment scheme such as the signal amplitude of the reverse power and any predetermined maximum or minimum values for various pulse parameters.

The reverse power signal can be used to detect fault conditions in the RF-power delivery system. In an ideal condition, when TX antenna 104 has perfectly matched impedance to the tissue that it contacts, the electromagnetic waves generated from the RF pulse generator 506 pass unimpeded from the TX antenna 104 into the body tissue. However, in real-world applications a large degree of variability may exist in the body types of users, types of clothing worn, and positioning of the antenna 104 relative to the body surface. Since the impedance of the antenna 104 depends on the relative permittivity of the underlying tissue and any intervening materials, and also depends on the overall separation distance of the antenna from the skin, in any given application there can be an impedance mismatch at the interface of the TX antenna 104 with the body surface. When such a mismatch occurs, the electromagnetic waves sent from the RF pulse generator 506 are partially reflected at this interface, and this reflected energy propagates backward through the antenna feed.

The dual directional coupler RF switch 223 may prevent the reflected RF energy propagating back into the amplifier 226, and may attenuate this reflected RF signal and send the attenuated signal as the reverse power signal to the feedback subsystem 212. The feedback subsystem 212 can convert this high-frequency AC signal to a DC level that can be sampled and sent to the controller subsystem 214. The controller subsystem 214 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 214 can measure the reflected-power ratio in real time, and according to preset thresholds for this measurement, the controller subsystem 214 can modify the level of RF power generated by the RF pulse generator 506. For example, for a moderate degree of reflected power the course of action can be for the controller subsystem 214 to increase the amplitude of RF power sent to the TX antenna 104, as would be needed to compensate for slightly non-optimum but acceptable TX antenna coupling to the body. For higher ratios of reflected power, the course of action can be to prevent operation of the RF pulse generator 506 and set a fault code to indicate that the TX antenna 104 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can lead to unwanted heating of internal components, and this fault condition means the system cannot deliver sufficient power to the implanted wireless neural stimulator and thus cannot deliver therapy to the user.

The controller 242 of the tissue stimulator 514 may transmit informational signals, such as a telemetry signal, through the antenna 238 to communicate with the RF pulse generator module 506 during its receive cycle. For example, the telemetry signal from the tissue stimulator 514 may be coupled to the modulated signal on the dipole antenna(s) 238, during the on and off state of the transistor circuit to enable or disable a waveform that produces the corresponding RF bursts necessary to transmit to the external (or remotely implanted) pulse generator module 506. The antenna(s) 238 may be connected to electrodes 254 (e.g., embodiments of the electrodes 108) in contact with tissue to provide a return path for the transmitted signal. An A/D (not shown) converter can be used to transfer stored data to a serialized pattern that can be transmitted on the pulse modulated signal from the internal antenna(s) 238 of the neural stimulator.

A telemetry signal from the implanted wireless tissue stimulator 514 may include stimulus parameters such as the power or the amplitude of the current that is delivered to the tissue from the electrodes. The feedback signal can be transmitted to the RF pulse generator module 506 to indicate the strength of the stimulus at the nerve bundle by means of coupling the signal to the implanted RX antenna 238, which radiates the telemetry signal to the external (or remotely implanted) RF pulse generator module 506. The feedback signal can include either or both an analog and digital telemetry pulse modulated carrier signal. Data such as stimulation pulse parameters and measured characteristics of stimulator performance can be stored in an internal memory device within the implanted tissue stimulator 514, and sent on the telemetry signal. The frequency of the carrier signal may be in the range of at 300 MHz to 8 GHz.

In the feedback subsystem 212, the telemetry signal can be down modulated using demodulator 222 and digitized by being processed through an analog to digital (A/D) converter 220. The digital telemetry signal may then be routed to a CPU 230 with embedded code, with the option to reprogram, to translate the signal into a corresponding current measurement in the tissue based on the amplitude of the received signal. The CPU 230 of the controller subsystem 214 can compare the reported stimulus parameters to those held in local memory 228 to verify that the tissue stimulator 514 delivered the specified stimuli to tissue. For example, if the tissue stimulator 514 reports a lower current than was specified, the power level from the RF pulse generator module 506 can be increased so that the implanted tissue stimulator 514 will have more available power for stimulation. The implanted tissue stimulator 514 can generate telemetry data in real time, for example, at a rate of 8 kbits per second. All feedback data received from the implanted tissue stimulator 514 can be logged against time and sampled to be stored for retrieval to a remote monitoring system accessible by the health care professional for trending and statistical correlations.

The sequence of remotely programmable RF signals received by the internal antenna(s) 238 may be conditioned into waveforms that are controlled within the tissue stimulator 514 by the control subsystem 242 and routed to the appropriate electrodes 254 that are placed in proximity to the tissue to be stimulated. For instance, the RF signal transmitted from the RF pulse generator module 506 may be received by RX antenna 238 and processed by circuitry, such as waveform conditioning circuitry 240, within the implanted wireless tissue stimulator 514 to be converted into electrical pulses applied to the electrodes 254 through electrode interface 252. In some implementations, the implanted tissue stimulator 514 contains between two to sixteen electrodes 254.

The waveform conditioning circuitry 240 may include a rectifier 244, which rectifies the signal received by the RX antenna 238. The rectified signal may be fed to the controller 242 for receiving encoded instructions from the RF pulse generator module 506. The rectifier signal may also be fed to a charge balance component 246 that is configured to create one or more electrical pulses based such that the one or more electrical pulses result in a substantially zero net charge at the one or more electrodes (that is, the pulses are charge balanced). The charge balanced pulses are passed through the current limiter 248 to the electrode interface 252, which applies the pulses to the electrodes 254 as appropriate.

The current limiter 248 insures the current level of the pulses applied to the electrodes 254 is not above a threshold current level. In some implementations, an amplitude (for example, current level, voltage level, or power level) of the received RF pulse directly determines the amplitude of the stimulus. In this case, it may be particularly beneficial to include current limiter 248 to prevent excessive current or charge being delivered through the electrodes, although current limiter 248 may be used in other implementations where this is not the case. Generally, for a given electrode having several square millimeters surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the limiter 248 acts as a charge limiter that limits a characteristic (for example, current or duration) of the electrical pulses so that the charge per phase remains below a threshold level (typically, a safe-charge limit).

In the event the implanted wireless tissue stimulator 514 receives a "strong" pulse of RF power sufficient to generate a stimulus that would exceed the predetermined safe-charge limit, the current limiter 248 can automatically limit or "clip" the stimulus phase to maintain the total charge of the phase within the safety limit. The current limiter 248 may be a passive current limiting component that cuts the signal to the electrodes 254 once the safe current limit (the threshold current level) is reached. Alternatively, or additionally, the current limiter 248 may communicate with the electrode interface 252 to turn off all electrodes 254 to prevent tissue damaging current levels.

A clipping event may trigger a current limiter feedback control mode. The action of clipping may cause the controller to send a threshold power data signal to the pulse generator 238. The feedback subsystem 212 detects the threshold power signal and demodulates the signal into data that is communicated to the controller subsystem 214. The controller subsystem 214 algorithms may act on this current-limiting condition by specifically reducing the RF power generated by the RF pulse generator, or cutting the power completely. In this way, the pulse generator 506 can reduce the RF power delivered to the body if the implanted wireless tissue stimulator 514 reports it is receiving excess RF power.

The controller 250 of the stimulator 205 may communicate with the electrode interface 252 to control various aspects of the electrode setup and pulses applied to the electrodes 254. The electrode interface 252 may act as a multiplex and control the polarity and switching of each of the electrodes 254. For instance, in some implementations, the wireless stimulator 506 has multiple electrodes 254 in contact with tissue, and for a given stimulus the RF pulse generator module 506 can arbitrarily assign one or more electrodes to 1) act as a stimulating electrode, 2) act as a return electrode, or 3) be inactive by communication of assignment sent wirelessly with the parameter instructions, which the controller 250 uses to set electrode interface 252 as appropriate. It may be physiologically advantageous to assign, for example, one or two electrodes as stimulating electrodes and to assign all remaining electrodes as return electrodes.

Also, in some implementations, for a given stimulus pulse, the controller 250 may control the electrode interface 252 to divide the current arbitrarily (or according to instructions from pulse generator module 506) among the designated stimulating electrodes. This control over electrode assignment and current control can be advantageous because in practice the electrodes 254 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T_start and terminated at a time T_final, and this time course may be synchronized across all stimulating and return electrodes; further, the frequency of repetition of this stimulus cycle may be synchronous for all the electrodes. However, controller 250, on its own or in response to instructions from pulse generator 238, can control electrode interface 252 to designate one or more subsets of electrodes to deliver stimulus waveforms with non-synchronous start and stop times, and the frequency of repetition of each stimulus cycle can be arbitrarily and independently specified.

For example, a stimulator having eight electrodes may be configured to have a subset of five electrodes, called set A, and a subset of three electrodes, called set B. Set A might be configured to use two of its electrodes as stimulating electrodes, with the remainder being return electrodes. Set B might be configured to have just one stimulating electrode. The controller 250 could then specify that set A deliver a stimulus phase with 3 mA current for a duration of 200 us followed by a 400 us charge-balancing phase. This stimulus cycle could be specified to repeat at a rate of 60 cycles per second. Then, for set B, the controller 250 could specify a stimulus phase with 1 mA current for duration of 500 us followed by a 800 us charge-balancing phase. The repetition rate for the set-B stimulus cycle can be set independently of set A, say for example it could be specified at cycles per second. Or, if the controller 250 was configured to match the repetition rate for set B to that of set A, for such a case the controller 250 can specify the relative start times of the stimulus cycles to be coincident in time or to be arbitrarily offset from one another by some delay interval.

In some implementations, the controller 250 can arbitrarily shape the stimulus waveform amplitude, and may do so in response to instructions from pulse generator 506. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 250 can increase or decrease the level of current at any time during the stimulus phase and/or during the charge-balancing phase. Thus, in some implementations, the controller 250 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, the tissue stimulator 514 may include a charge balancing component 246. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units uC/cm.sup.2. In order to avoid the irreversible electrochemical reactions such as pH change, electrode dissolution as well as tissue destruction, no net charge should appear at the electrode-electrolyte interface, and it is generally acceptable to have a charge density less than 30 uC/cm.sup.2. Biphasic stimulating current pulses ensure that no net charge appears at the electrode after each stimulation cycle and the electrochemical processes are balanced to prevent net dc currents. The tissue stimulator 514 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or current, called the cathodic phase of the waveform. Stimulating electrodes may have both cathodic and anodic phases at different times during the stimulus cycle. An electrode that delivers a negative current with sufficient amplitude to stimulate adjacent neural tissue is called a "stimulating electrode." During the stimulus phase the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 246 uses a blocking capacitor(s) placed electrically in series with the stimulating electrodes and body tissue, between the point of stimulus generation within the stimulator circuitry and the point of stimulus delivery to tissue. In this manner, a resistor-capacitor (RC) network may be formed. In a multi-electrode stimulator, one charge-balance capacitor(s) may be used for each electrode or a centralized capacitor(s) may be used within the stimulator circuitry prior to the point of electrode selection. The RC network can block direct current (DC), however it can also prevent low-frequency alternating current (AC) from passing to the tissue. The frequency below which the series RC network essentially blocks signals is commonly referred to as the cutoff frequency, and in one embodiment the design of the stimulator system may ensure the cutoff frequency is not above the fundamental frequency of the stimulus waveform. In this embodiment of the present invention, the wireless stimulator may have a charge-balance capacitor with a value chosen according to the measured series resistance of the electrodes and the tissue environment in which the stimulator is implanted. By selecting a specific capacitance value the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the wireless tissue stimulator 514 may create a drive-waveform envelope that follows the envelope of the RF pulse received by the receiving dipole antenna(s) 238. In this case, the RF pulse generator module 506 can directly control the envelope of the drive waveform within the wireless tissue stimulator 514, and thus no energy storage may be required inside the stimulator itself. In this implementation, the stimulator circuitry may modify the envelope of the drive waveform or may pass it directly to the charge-balance capacitor and/or electrode-selection stage.

In some implementations, the implanted tissue stimulator 514 may deliver a single-phase drive waveform to the charge balance capacitor or it may deliver multiphase drive waveforms. In the case of a single-phase drive waveform, for example, a negative-going rectangular pulse, this pulse includes the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the stimulator facilitates the discharge of the charge-balance capacitor. In some implementations, using a passive discharge phase, the capacitor may allow virtually complete discharge prior to the onset of the subsequent stimulus pulse.

In the case of multiphase drive waveforms the tissue stimulator 514 may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is controlled by the amplitude and timing of RF pulses from the RF pulse generator module 506, and in others this control may be administered internally by circuitry onboard the tissue stimulator 514, such as controller 250. In the case of onboard control, the amplitude and timing may be specified or modified by data commands delivered from the pulse generator module 506.

Other embodiments of antenna assemblies and tissue stimulation systems are within the scope of the following claims.

What is claimed is:

1. An assembly comprising:
an antenna configured to transmit a signal to a wireless stimulator implanted within a body;
a substrate supporting the antenna and including one or more through openings;
a housing surrounding the antenna and the substrate; and
one or more fasteners configured to attach to a wearable article for positioning the antenna adjacent the body on which the wearable article is worn, each of the one or more fasteners passing through the housing and passing through respective ones of the one or more through openings in the substrate.

2. The assembly of claim 1, further comprising a cable electrically coupled to the antenna, the cable extending out of the housing.

3. The assembly of claim 2, further comprising a connector coupled to the cable, the connector configured to be connected to a pulse generator configured to send signals to and receive signals from the antenna.

4. The assembly of claim 1, wherein the substrate includes a printed circuit board and the antenna is disposed on the printed circuit board.

5. The assembly of claim 1, wherein the substrate includes a support region on which the antenna is disposed, wherein the support region has a shape that is formed complimentary to a shape of the antenna.

6. The assembly of claim 5, wherein the one or more through openings are outside of the support region of the substrate.

7. The assembly of claim 1, wherein the one or more fasteners include a pop rivet snap, a hook and loop fastener, a magnet, a pin, a hanging slot, or a friction clasp.

8. The assembly of claim 1, wherein the antenna is formed of a flexible conductive layer with a symmetrical shape.

9. The assembly of claim 1, wherein the antenna is formed of two disconnected portions and a shape of one of the two portions is a mirror image of another one of the two portions.

10. The assembly of claim 1, wherein the housing includes a sleeve, a flexible material, a molded fabric, or a polymer.

11. The assembly of claim 1, wherein a number of the one or more fasteners is four.

12. An assembly comprising:
a printed circuit board upon which an antenna is disposed, the printed circuit board including one or more through openings;
a housing surrounding the printed circuit board; and
one or more fasteners configured to attach to a wearable article for positioning the antenna adjacent a body on which the wearable article is worn, each of the one or more fasteners passing through the housing and passing through respective ones of the one or more through openings in the printed circuit board.

13. The assembly of claim 12, wherein the antenna is configured to transmit a signal to a wireless stimulator implanted within the body.

14. The assembly of claim 12, wherein the printed circuit board includes a support region on which the antenna is disposed, wherein the support region has a shape that is formed complimentary to a shape of the antenna.

15. The assembly of claim 14, wherein the one or more through openings are outside of the support region of the printed circuit board.

16. The assembly of claim 12, wherein the one or more fasteners include a pop rivet snap, a hook and loop fastener, a magnet, a pin, a hanging slot, or a friction clasp.

17. A stimulation system, comprising:
a pulse generator configured to generate a signal; and
an assembly comprising:
an antenna coupled to the pulse generator and configured to transmit the signal to a wireless stimulator implanted within a body;
a substrate supporting the antenna and including one or more through openings;
a housing surrounding the antenna and the substrate; and
one or more fasteners configured to attach to a wearable article for positioning the antenna adjacent the body on which the wearable article is worn, each of the one or more fasteners passing through the housing and passing through respective ones of the one or more through openings in the substrate.

18. The stimulation system of claim 17, wherein the substrate includes a printed circuit board and the antenna is disposed on the printed circuit board.

19. The stimulation system of claim 17, further comprising a cable electrically coupled between the pulse generator and the antenna.

20. The stimulation system of claim 17, wherein the one or more fasteners include a pop rivet snap, a hook and loop fastener, a magnet, a pin, a hanging slot, or a friction clasp.

* * * * *